United States Patent
Secchi et al.

(10) Patent No.: US 8,477,185 B2
(45) Date of Patent: Jul. 2, 2013

(54) SYSTEM FOR THE ANGULAR ORIENTATION AND DETECTION OF CONTAINERS IN LABELLING MACHINES

(75) Inventors: Antonio Secchi, Pully (CH); Giuseppe Femia, Pully (CH)

(73) Assignee: Sidel Holdings & Technology S.A., Pully (CH)

( * ) Notice: Subject to any disclaimer, the term of this patent is extended or adjusted under 35 U.S.C. 154(b) by 380 days.

(21) Appl. No.: 12/744,834

(22) PCT Filed: Nov. 24, 2008

(86) PCT No.: PCT/IT2008/000721
§ 371 (c)(1),
(2), (4) Date: Sep. 15, 2010

(87) PCT Pub. No.: WO2009/072157
PCT Pub. Date: Jun. 11, 2009

(65) Prior Publication Data
US 2011/0001817 A1  Jan. 6, 2011

(30) Foreign Application Priority Data
Dec. 3, 2007 (IT) ............................... MI2007A2267

(51) Int. Cl.
*B65C 9/06* (2006.01)
*B65B 3/00* (2006.01)

(52) U.S. Cl.
USPC ........................................ 348/86; 348/E7.85

(58) Field of Classification Search
None
See application file for complete search history.

(56) References Cited

U.S. PATENT DOCUMENTS

| | | | | |
|---|---|---|---|---|
| 6,618,495 | B1* | 9/2003 | Furnas | 382/142 |
| 7,013,624 | B2* | 3/2006 | Zwilling | 53/544 |
| 7,331,152 | B2* | 2/2008 | Menke | 53/67 |
| 2005/0117149 | A1* | 6/2005 | Grindinger et al. | 356/239.4 |
| 2006/0249242 | A1* | 11/2006 | Sernesi et al. | 156/86 |
| 2008/0056556 | A1* | 3/2008 | Eller et al. | 382/142 |
| 2008/0308727 | A1* | 12/2008 | Boguslavsky et al. | 250/307 |
| 2009/0050267 | A1* | 2/2009 | Conlon et al. | 156/312 |

FOREIGN PATENT DOCUMENTS

| | | |
|---|---|---|
| DE | 10 2005 041 497 A1 | 3/2007 |
| EP | 1 510 809 A1 | 3/2005 |
| EP | 1 777 163 A1 | 4/2007 |
| GB | 2 334 576 A | 8/1999 |
| JP | 2001-50898 A | 2/2001 |
| WO | WO 2008/072070 * | 6/2008 |
| WO | WO 2008/072070 A2 | 6/2008 |

* cited by examiner

*Primary Examiner* — Gims Philippe
*Assistant Examiner* — Reza Aghevli
(74) *Attorney, Agent, or Firm* — Dickstein Shapiro LLP

(57) ABSTRACT

A system for the angular orientation and detection of containers being processed in labelling machines. More particularly, the present invention relates to a system for the detection and angular orientation of containers in labelling machines with a rotating turntable for handling the containers. The turntable is provided with a plurality of motor-driven pans which support and handle the containers. Four image cameras are controlled so as to acquire a set of four images which replicate the container image throughout the side surface or perimeter of the container.

17 Claims, 3 Drawing Sheets

SYSTEM FOR THE ANGULAR ORIENTATION AND DETECTION OF CONTAINERS IN LABELLING MACHINES

This is a 371 of International Application No. PCT/IT2008/000721, filed on Nov. 24, 2008, which claims priority to Italian application No. MI2007A002267, filed on Dec. 3, 2007.

The present invention relates to a system for the angular orientation and detection of containers being processed in labelling machines.

The labelling operation of containers in high speed automatic labelling machines sets out the problem of the correct positioning of the label. Such machines usually comprise turntables, on which a plurality of pans is mounted, which are intended to support and handle the containers to be labelled, together with jacks engaging the container upper end in order to hold it in an upright position on the pan. Such pans are motor-driven, so as to allow the rotation thereof and of the containers they support around the vertical axis thereof. This operation serves to the label application, which label will thus wrap around the container side surface during the rotation thereof.

In a machine as the one described herein, which operates at a high speed, the container angular orientation according to a preset pattern is critical for a smooth operation of the machine.

In the conventional plants, the container correct orientation is achieved by a timing of a mechanical type which, however, often turns out to be not very reliable.

The angular orientation and detection system of the containers being the object of the invention, as set forth in the annexed claims, the contents of which are an integral part of the present description, allows a control and retiming of the container angular position of an electronic type, and it is characterized by a high accuracy and reliability.

Further characteristics and the advantages of the present invention will be more clearly understood from the description of some exemplary embodiments, given herein below by way of illustrative and non-limiting example, with reference to the following Figures.

Figure 1:
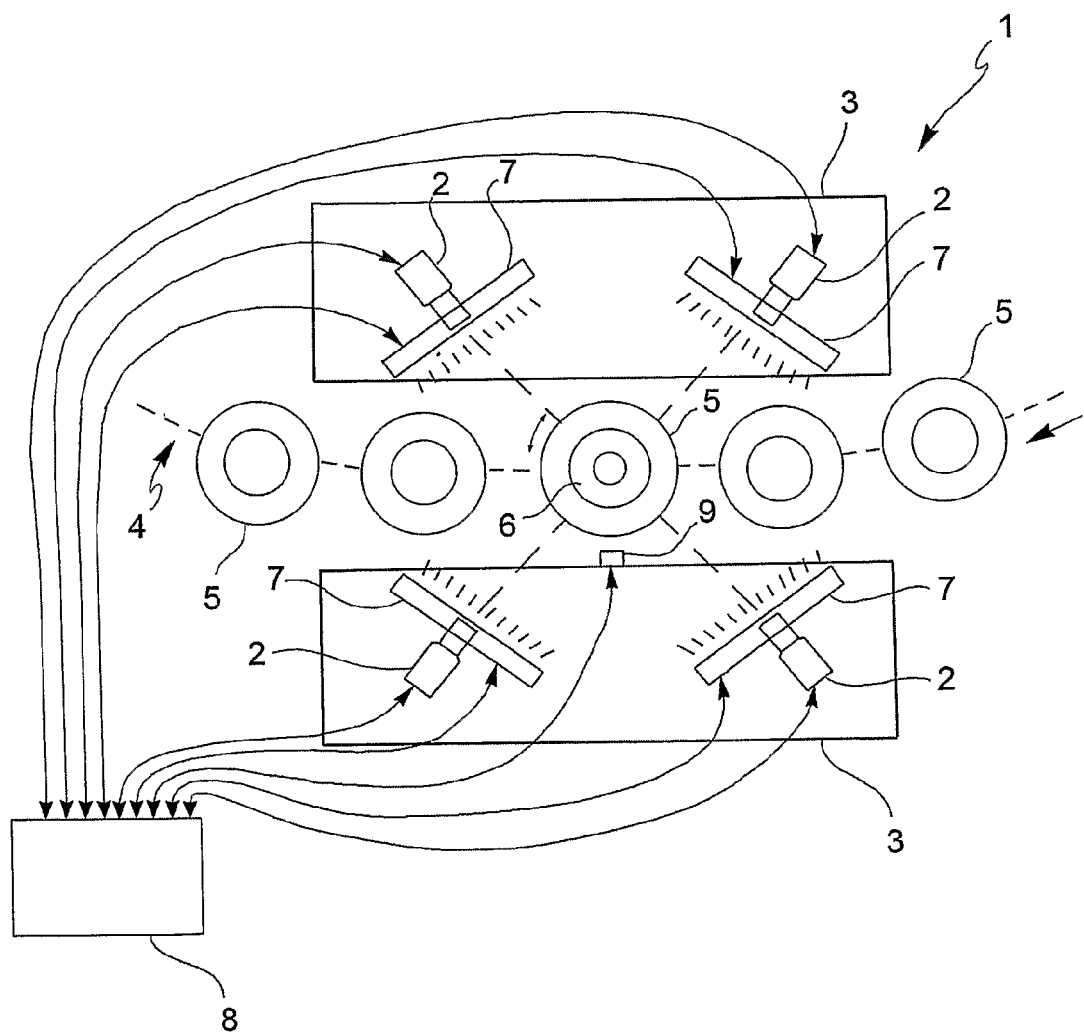
FIG. 1 represents a schematic top view of a detail of the system which is the object of the invention.
Figure 2:
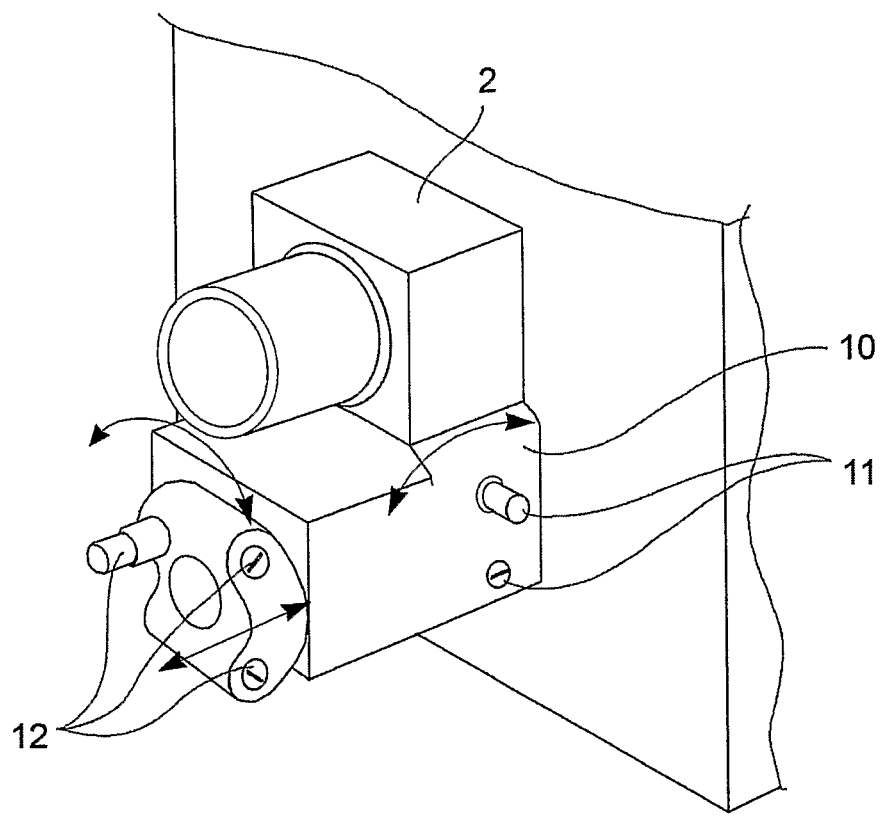
FIG. 2 represents a detail of a camera of the system which is the object of the invention.

With reference to the Figures, the orientation and detection system of the containers of the invention will be now described, generally indicated with the reference numeral 1.

The system 1 comprises four cameras 2, or other optical means for the image acquisition, geometrically arranged at the vertexes of a square and so oriented as to result to be facing in pairs along the diagonals of the square. Such cameras 2 are housed in pairs within housings 3, preferably made of metallic material, but having walls of a transparent material, preferably anti-burglary glasses, at least at the cameras 2 visual field.

The two housings 3 are arranged inside and outside, respectively, a rotating turntable 4 for the handling of containers, having a plurality of motor-driven pans 5 which support and handle the containers 6. The housings are arranged so that each container 6, during the travel thereof along the turntable 4 perimeter, will pass at the intersection of the diagonals joining the cameras 2 in pairs.

Suitable illuminating means 7 are located at each camera 2, so as to illuminate the visual field thereof, along the diagonals joining the same cameras 2. Such illuminating means 7 are preferably white led bar illuminators. Preferably, the illuminating means 7 are arranged beneath the cameras 2.

A photocell 9 is located at the vertical axis which passes through the intersection of the diagonals joining the cameras 2 in pairs, in an overhead position to the container. Such photocell 9 reads the presence of the container which is in the correct position by intercepting the upper jack for the setting of the same container.

The four cameras 2, the respective illuminating means 7, and the photocell 9 are operatively connected to a control and driving unit 8 which, via a suitable software, provides for the system actuation as described below.

The cameras 2 are mounted on supports 10. The supports 10 comprise adjustment means 11 for the top-down horizontally pivoted adjustment of the camera; and adjustment means 12 for the side-to-side horizontally pivoted adjustment, as well as for the forward-backward translation (focusing). In this manner, it is possible to achieve a fine adjustment of the camera 2 position, thus the correct aiming of the container. Such initial aiming is extremely important, since it dictates the system 1 operation. The system software provides reference elements which allow framing the container and adjusting the camera so as to align the system reference elements to the prompt elements which are present on the container.

The above-described system works as follows.

The containers have prompt elements which can be composed of a series of wrinkles or dots in the proximity of the bottom, or writings, or other indicia. Such prompt elements are then used for the correct timing of the container on the pan. The containers arrive on the several pans in a completely random angular position, therefore a timing thereof is required, i.e. it is necessary to angularly orientating all of them in the same position before they reach the labelling step.

Thereby, the four cameras 2, or other optical means of image acquisition according to the invention, are adapted to take an image of the bottle throughout side surface. More precisely, four images will be taken for each container, one for each camera 2. The set of four images relative to each container is analyzed by the control and driving unit 8 according to the following pattern:

a) Identifying the prompt elements on the container under examination;
b) Comparing the set of acquired images to a control set or calibration table;
c) Calculating the deviation of said prompt elements in the container under examination relative to said control set or calibration table;
d) Sending a command to the motor of the pan which supports the container under examination, so as to rotate said pan by an angle so as to accommodate said container position to the reference position.

In order to achieve a correct image acquisition, it is critical that the cameras 2 visual field is properly illuminated. According to the invention, the illuminating means 7 described above are associated with each camera 2. However, since such illuminating means 7 are facing in pairs, the actuation of each of them would result in a blinding of the camera 2 opposite thereto, in particular with glass containers.

In order to obviate this drawback, the control and driving unit 8:

sends an image acquisition command to a first camera 2 following the container presence signal sent by the photocell 9;

concomitantly, sends the turn on command to the illuminating means 7 related to said camera 2 in acquisition mode, and to the two illuminating means 7 lateral thereto, while keeping the illuminating means 7 opposite the camera 2 in acquisition mode as off;

repeats said two first steps with the successive cameras 2 according to a preset temporal sequence until the acquisition of the four images of the container under examination.

The software of the system 1 according to the invention allows tailoring to any container formats, through said calibration table, which is created during a suitable calibration step, comprising:
 i) Detecting the already-labelled container diameter and edges, the prompt elements which are present on the container, and the image light/dark contrast;
 ii) Acquiring a first set of four images of the container being tested;
 iii) Rotating the pan with the container being tested by 10°, and acquiring a second set of four images;
 iv) Repeating the operation of the step iii) 35 times until completing a 360° rotation of the container being tested;
 v) Identifying the label starting point in the sets of acquired images, calculating, for each of them, the distance X between edge container and label starting point, and associating the corresponding rotation angle to said distance X;
 vi) Creating a calibration table from such data.

Figure 3:
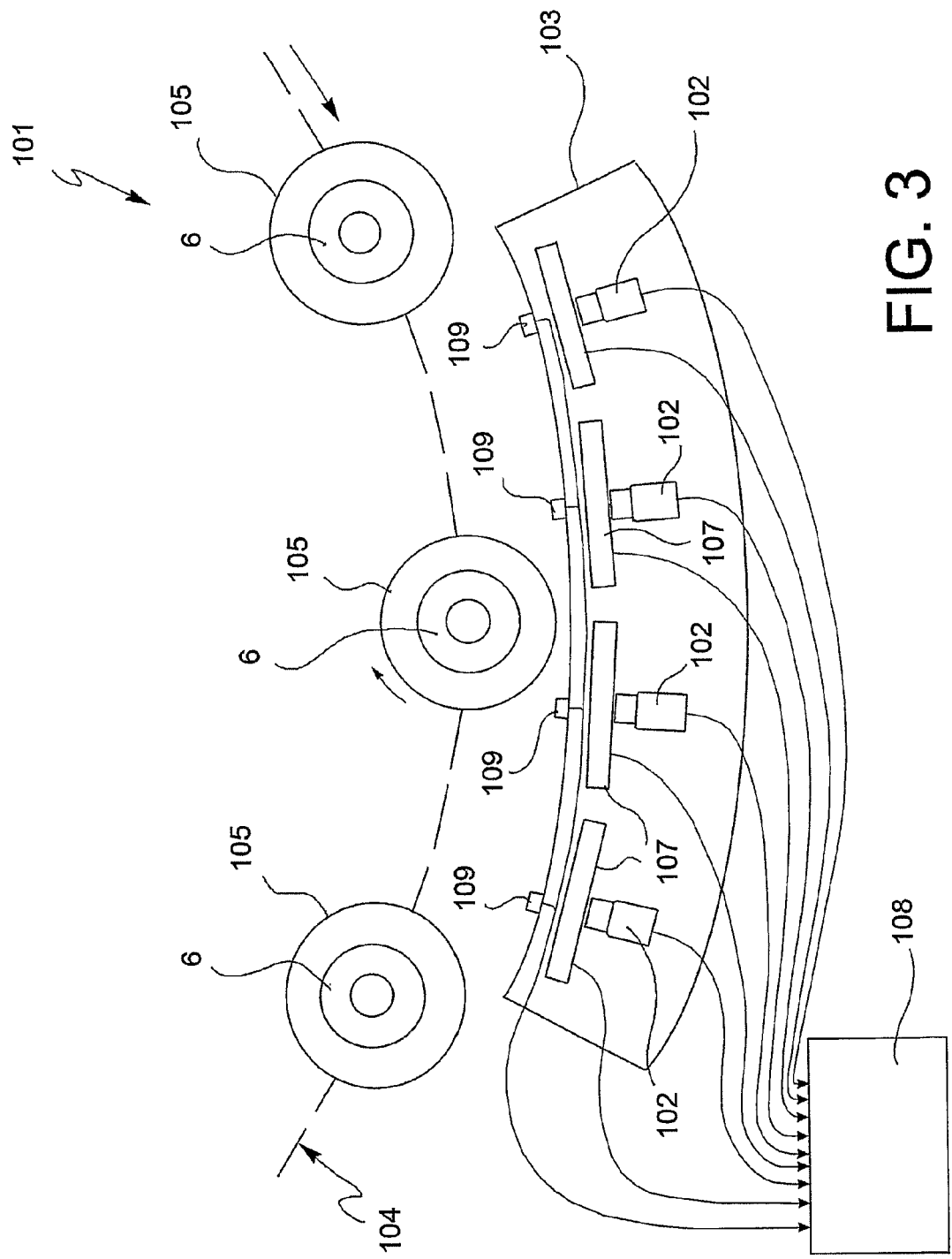
FIG. 3 represents a schematic top view of a detail of the system which is the object of the invention, according to a different embodiment.

According to a different embodiment of the invention, as shown in FIG. 3, the four cameras 102, and the four illuminating means 107 related thereto, are all arranged externally relative to the turntable 4, and are orientated along an arc of circle having essentially the same radius of curvature as the turntable 4. Again in this case, cameras 102 and illuminating means 107 can be housed within a suitable housing 103, which is totally similar to the housings 3 previously described.

A photocell 109 is associated with each camera, arranged aligned with the visual axis of the camera 102 related thereto, in an overhead position relative to the container 6. Such photocell 109 reads the presence of the container in the correct position by intercepting the upper jack for the setting of the same container.

The four cameras 102, the respective illuminating means 107, and the photocells 109 are operatively connected to a control and driving unit 108 which, through suitable software, provides for the system actuation as described below.

The system 101 functioning according to this different embodiment is essentially the same as the one described above as regards the analysis operation of the images and the timing of the container 6, while it distinguishes from that for the image acquisition step, due to the cameras 102 different arrangement.

In particular, in this embodiment the control and driving unit 108:
 m) sends an image acquisition command to a first camera 102 following the container presence signal by the photocell 109 associated with said first camera 102;
 n) concomitantly, it sends the turn on command to the illuminating means 107 related to said camera in acquisition mode, while keeping the remaining illuminating means 107 off;
 o) rotates the pan which supports the container 6 under examination by 90°;
 p) repeats the steps m) and n) with the successive camera 102;
 q) repeats the steps o) and p) with the two remaining cameras 102, according to a preset temporal sequence until the acquisition of the four images of the container under examination.

The advantages of the angular orientation and detection system of containers according to the invention are clearly understood by those skilled in the art, and can be summarized in a considerable adjustment accuracy (accuracy of the order of 1 mm or less), implementation easiness, and installation and maintenance economy.

It shall be understood that only some particular embodiments of the present invention have been described, to which those skilled in the art will be able to make all the required modifications for the accommodation thereof to particular applications, without anyhow departing from the scope of protection of the present invention.

The invention claimed is:

1. A system for the detection and angular orientation of containers in labelling machines comprising a rotating turntable for the handling of said containers, said turntable being provided with a plurality of motor-driven pans which support and handle said containers, and four image acquisition optical means, said four optical means being controlled so as to acquire a set of four images which replicate the container image along all the perimeter thereof,
 wherein said four image acquisition optical means are oriented so as to be facing in pairs along visual axes, so that each container during the travel thereof along the turntable perimeter, passes at an intersection of the visual axes joining in pairs.

2. The system according to claim 1, wherein said four image acquisition optical means are geometrically arranged at the vertexes of a square and are facing in pairs along the diagonals of the square.

3. The system according to any claim 1, wherein said image acquisition optical means are cameras.

4. The system according to any claim 1, comprising illumination means located at each image acquisition optical means so as to illuminate said optical means visual field.

5. The system according to claim 4, wherein said illuminating means are white led bar illuminators.

6. The system according to claim 4, wherein said illuminating means are located beneath said image acquisition optical means.

7. The system according to claim 1, wherein said optical means are housed within housings.

8. The system according to claim 7, wherein said housings are made of metallic material, but have walls in transparent material, preferably anti-burglary glasses, at least at said image acquisition optical means visual field.

9. The system according to claim 1, wherein a photocell is positioned at the vertical axis which passes through the intersection of the diagonals joining the image acquisition optical means in pairs, in an overhead position relative to the container.

10. The system according to claim 9, wherein said photocell reads the presence of the container in correct position by intercepting the upper jack for holding the same container.

11. The system according to claim 1, wherein said image acquisition optical means are mounted on supports comprising adjustment means for the top-down horizontally pivoted adjustment of the camera; and adjustment means for the side-to-side horizontally pivoted adjustment and the forward-backward translation for the focusing.

12. The system according to claim 1, wherein said four image acquisition optical means, said illuminating means, and said photocells are operatively connected to a control and driving unit on which a software runs, which provides for the acquisition and analysis of a set of four images for each container under examination.

13. The system according to claim 12, wherein the control and driving unit: sends an image acquisition command to a first optical means following the container presence signal by the photocell; concomitantly sends the turn on command to the illuminating means relative to said optical means in acquisition mode, and to the two illuminating means lateral thereto, while keeping the illuminating means opposite the optical means in acquisition off; repeats said two first steps with the successive optical means according to a preset temporal sequence until the acquisition of the four images of the container under examination.

14. The system according to claim 12, wherein said control and driving unit analyzes said set of four images of the container under examination according to the following pattern:
   a) Identifying the prompt elements of the container under examination;
   b) Comparing the set of acquired images with a control set or calibration table;
   c) Calculating the deviation of said prompt elements in the container (β) under examination relative to said control set or calibration table;
   d) Sending a command to the motor of the pan which supports the container under examination so as to rotate said pan by an angle such as to match the position of said container to the reference position.

15. The system according to claim 12, wherein said calibration table is created during a calibration step, which comprises:
   i) Detecting the already-labelled container diameter and edges, the prompt elements present on the container, and the image light/dark contrast;
   ii) Acquiring a first set of four images of the container being tested;
   iii) Rotating the pan with the container being tested by 10°, and acquiring a second set of four images;
   iv) Repeating the operation of the step iii) 35 times until completing a 360° rotation of the container being tested;
   v) Identifying the label starting point in the set of acquired images, calculating, for each of them, the distance X between container edge and label starting point, and associating the corresponding rotation angle to said distance X;
   vi) Creating a calibration table from such data.

16. The system according to claim 12, wherein said software provides for reference elements which allow framing the container and adjusting the camera so as to align the system reference elements to the prompt elements which are present on the container.

17. The system according to claim 2, wherein said image acquisition optical means are arranged in pairs, respectively, outside and inside said turntable.

* * * * *